United States Patent
Min et al.

(10) Patent No.: US 7,155,282 B1
(45) Date of Patent: Dec. 26, 2006

(54) AUTOMATIC SENSITIVITY CONTROL AND METHOD FOR USE IN AN IMPLANTABLE CARDIAC STIMULATION DEVICE

(75) Inventors: Xiaoyi Min, Thousand Oaks, CA (US); Gene A. Bornzin, Simi Valley, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 434 days.

(21) Appl. No.: 10/719,307

(22) Filed: Nov. 21, 2003

(51) Int. Cl.
  *A61N 1/362* (2006.01)
(52) U.S. Cl. .................................................. 607/28
(58) Field of Classification Search ............. 607/9, 607/11, 18, 25, 27, 28
  See application file for complete search history.

(56) References Cited

U.S. PATENT DOCUMENTS

| | | | |
|---|---|---|---|
| 4,708,144 A | 11/1987 | Hamilton et al. | 128/419 PG |
| 4,766,902 A | 8/1988 | Schroeppel | 128/419 PG |
| 4,768,511 A | 9/1988 | DeCote, Jr. | 128/419 PG |
| 5,269,300 A | 12/1993 | Kelly et al. | 607/4 |
| 5,339,820 A | 8/1994 | Henry et al. | 128/696 |
| 5,365,932 A | 11/1994 | Greenhut | 128/696 |
| 5,685,315 A | 11/1997 | McClure et al. | 128/708 |
| 5,755,738 A | 5/1998 | Kim et al. | 607/9 |
| 5,913,880 A | 6/1999 | Vonk | 607/27 |
| 5,957,857 A | 9/1999 | Hartley | 600/521 |
| 6,112,119 A | 8/2000 | Schuelke et al. | 607/9 |
| 6,625,490 B1 | 9/2003 | McClure et al. | 607/9 |

FOREIGN PATENT DOCUMENTS

| | | |
|---|---|---|
| EP | 1072284 A2 | 1/2001 |
| WO | WO 99/21612 | 6/1999 |

*Primary Examiner*—Scott M. Getzow

(57) ABSTRACT

A threshold sensing control for use in an implantable cardiac stimulation device controls the sensing of cardiac activity during a current cardiac cycle of a heart while avoiding sensing a T wave. The system includes a sensing circuit that senses cardiac activity of the heart during a cardiac cycle preceding the current cardiac cycle, a detector that measures selected T wave and R wave characteristics of the cardiac activity and a control circuit that varies the sensing threshold based upon the measured selected R wave and T wave characteristics. The sensing threshold control may be implemented for both intrinsic and paced beats.

20 Claims, 5 Drawing Sheets

AUTOMATIC SENSITIVITY CONTROL AND METHOD FOR USE IN AN IMPLANTABLE CARDIAC STIMULATION DEVICE

FIELD OF THE INVENTION

The present invention generally relates to an implantable cardiac stimulation device. The present invention more particularly relates to such a device and method providing automatic sensitivity control.

BACKGROUND

Combined implantable ventricular defibrillator and pacemaker stimulation devices are well known in the art. Such devices permit a heart to be paced for treating bradycardia, for example, while also detecting for ventricular fibrillation and ventricular tachycardia and applying defibrillating electrical energy, cardioversion shocks or antitachycardia pacing pulses to the heart when fibrillation or tachycardia is detected.

One problem that must be addressed in such devices is the need to reliably sense R waves. To this end, implantable cardiac devices generally include an automatic sensing control. The aim of such control is to maintain the sensing threshold low enough (sensitive enough) for detecting low amplitude R wave electrical activity of the heart (as may be present during fibrillation) while avoiding over-sensing which could result in a T wave or noise being sensed by the device and mistaken for an R wave.

Automatic sensing control has been performed by first establishing a ventricular refractory period (VREF) upon sensing an R wave and continuing the VREF for a predetermined time such as 100 to 140 milliseconds. Following the VREF, the sensing threshold is set at an initial level and then decreased thereafter from the initial threshold level to a minimum threshold level where it is held until the next paced or sensed event. The initial threshold, refractory period, threshold decay rate, and minimum threshold are selected so that the threshold is above the amplitude of the T waves or noise when they occur.

Even though present sensing controls have provided improved performance in rejecting far field signals and T waves in the sensing of R waves problems of inappropriate sensing and detection still exist. This can result in delivery of inappropriate therapies and significant patient morbidity.

Unfortunately, existing sensing controls still require programming to fix initial threshold, refractory period and threshold decay rate values. Unfortunately, these methods do not account for drifting of T wave amplitude and location. T wave amplitude and location can vary from patient to patient or with the same patent as the status of the patient's disease changes or even with changes in heart rate. This can cause a T wave to be present with an amplitude which exceeds a sensing threshold and thus be mistakenly detected as an R wave.

Thus, what is needed is an automated sensing control which takes T wave characteristics into account when controlling the sensing threshold.

SUMMARY

What is described herein is an implantable cardiac stimulation device comprising a sensing circuit that senses cardiac activity of a heart, the sensing circuit having a sensing threshold and a pulse generator that applies electrical energy to the heart in response to the sensed cardiac activity of the heart. The device further comprise a threshold control including a detector that determines a plurality of morphological characteristics of the cardiac activity and that varies the sensing threshold of the sensing circuit in response to the determined morphological characteristics of the cardiac activity.

The sensing circuit may be configured to sense ventricular activity and the plurality of morphological characteristics may include T wave characteristics. The T wave characteristics may include T wave amplitude and/or T wave location. The detector may further determine a plurality of R wave characteristics of the cardiac activity and the threshold control may vary the sensing threshold in response to the determined T wave characteristics and the determined R wave characteristics. The R wave characteristics include R wave amplitude and/or R wave location.

The detector may determine the morphological characteristics of intrinsic cardiac activity.

The detector may further determine the morphological characteristics of paced cardiac activity. The threshold control may compare determined morphological characteristics of paced cardiac activity to determined morphological characteristics of intrinsic cardiac activity prior to varying the sensing threshold. The morphological characteristics of intrinsic activity may be averaged for the comparison. The threshold control may compare most recently determined morphological characteristics to prior averaged determined morphological characteristics prior to varying the sensing threshold. To control the sensing threshold, the threshold control may provide a starting sensing threshold responsive to the determined morphological characteristics. The threshold control may further provide a refractory period responsive to the determined morphological characteristics and the starting sensing threshold may be implemented after the refractory period. The threshold control preferably linearly varies the sensing threshold from the starting sensing threshold to a minimum threshold.

The threshold control may vary the sensing threshold during a current cardiac cycle responsive to morphological characteristics of cardiac activity of a cardiac cycle preceding the current cardiac cycle.

The threshold control varies the sensing threshold during a current cardiac cycle responsive to averaged morphological characteristics of cardiac activity of cardiac cycles preceding the current cardiac cycle.

The sensing circuit may be an atrial sensing circuit that senses atrial activity and the threshold control may vary the sensing threshold to preclude sensing of far field R waves by the atrial sensing circuit. Here, the morphological characteristics preferably include far field R wave amplitude and R wave location.

In at least one illustrative embodiment, an implantable cardiac stimulation device comprises a sensing circuit having a threshold that senses cardiac activity of a heart. The device further comprises a pulse generator that applies electrical energy to the heart in response to the sensed cardiac activity of the heart and a threshold control including a detector that determines a plurality of T wave characteristics and R wave characteristics of the cardiac activity and that varies the sensing threshold of the sensing circuit in response to the determined T wave and R wave characteristics to avoid sensing T waves of the cardiac activity.

In yet another embodiment, a method of controlling sensing threshold of an implantable cardiac stimulation device. The method includes the steps of sensing cardiac activity of the heart, measuring a plurality of morphological characteristics of the sensed cardiac activity, and varying the sensing threshold based upon the measured morphological characteristics.

BRIEF DESCRIPTION OF THE DRAWINGS

Further features and advantages of the illustrative embodiments may be more readily understood by reference to the following description taken in conjunction with the accompanying drawings, in which.

DESCRIPTION OF THE PREFERRED EMBODIMENTS

The following description is of the best mode presently contemplated for the implantable stimulation device. This description is not to be taken in a limiting sense but is made merely for the purpose of describing the general principles of the implantable stimulation device. The scope of the invention should be ascertained with reference to the issued claims. In the description that follows, like numerals or reference designators will be used to refer to like parts or elements throughout.

Figure 1:
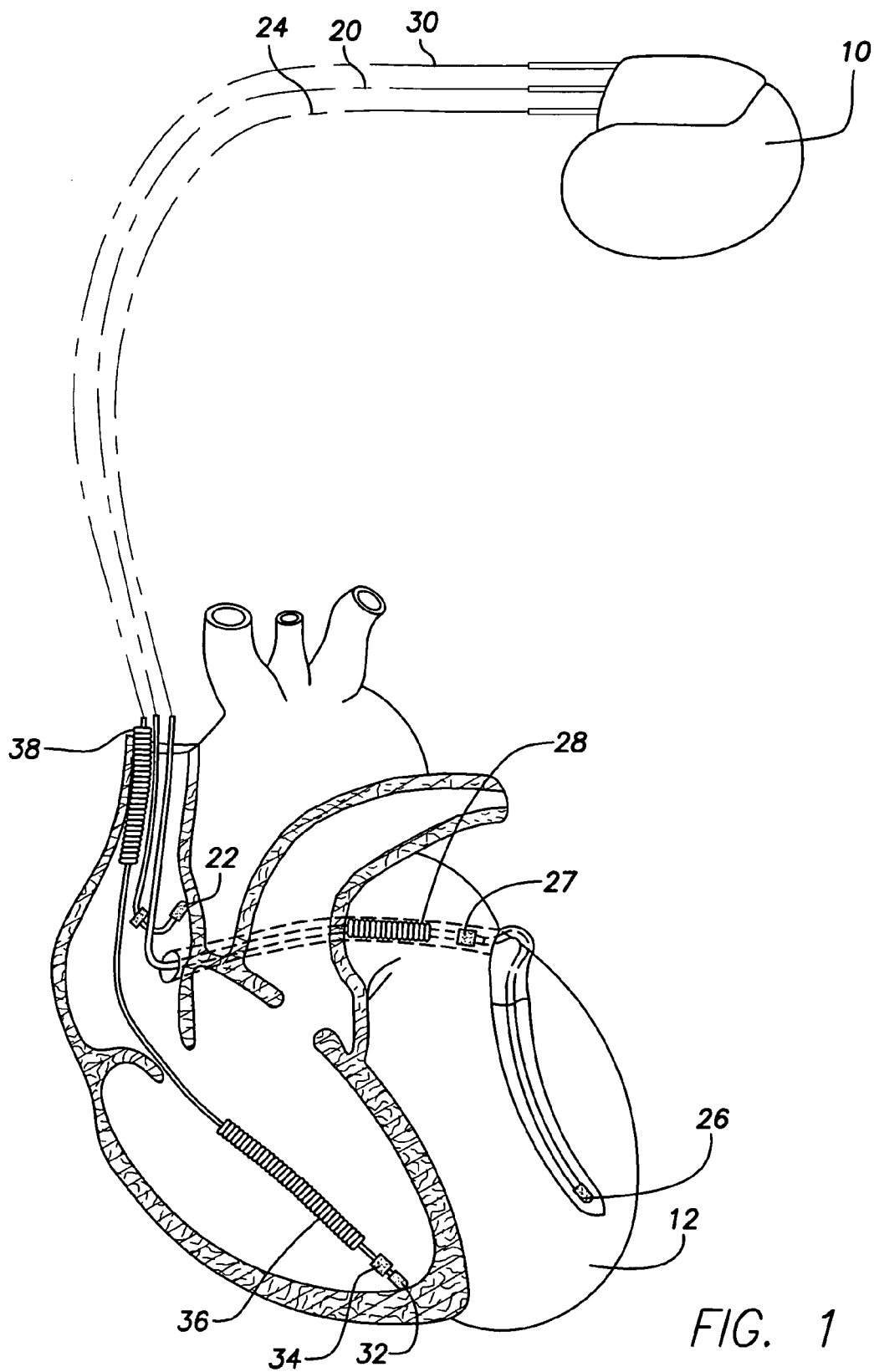
FIG. 1 is a simplified diagram illustrating one embodiment of an implantable stimulation device shown with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
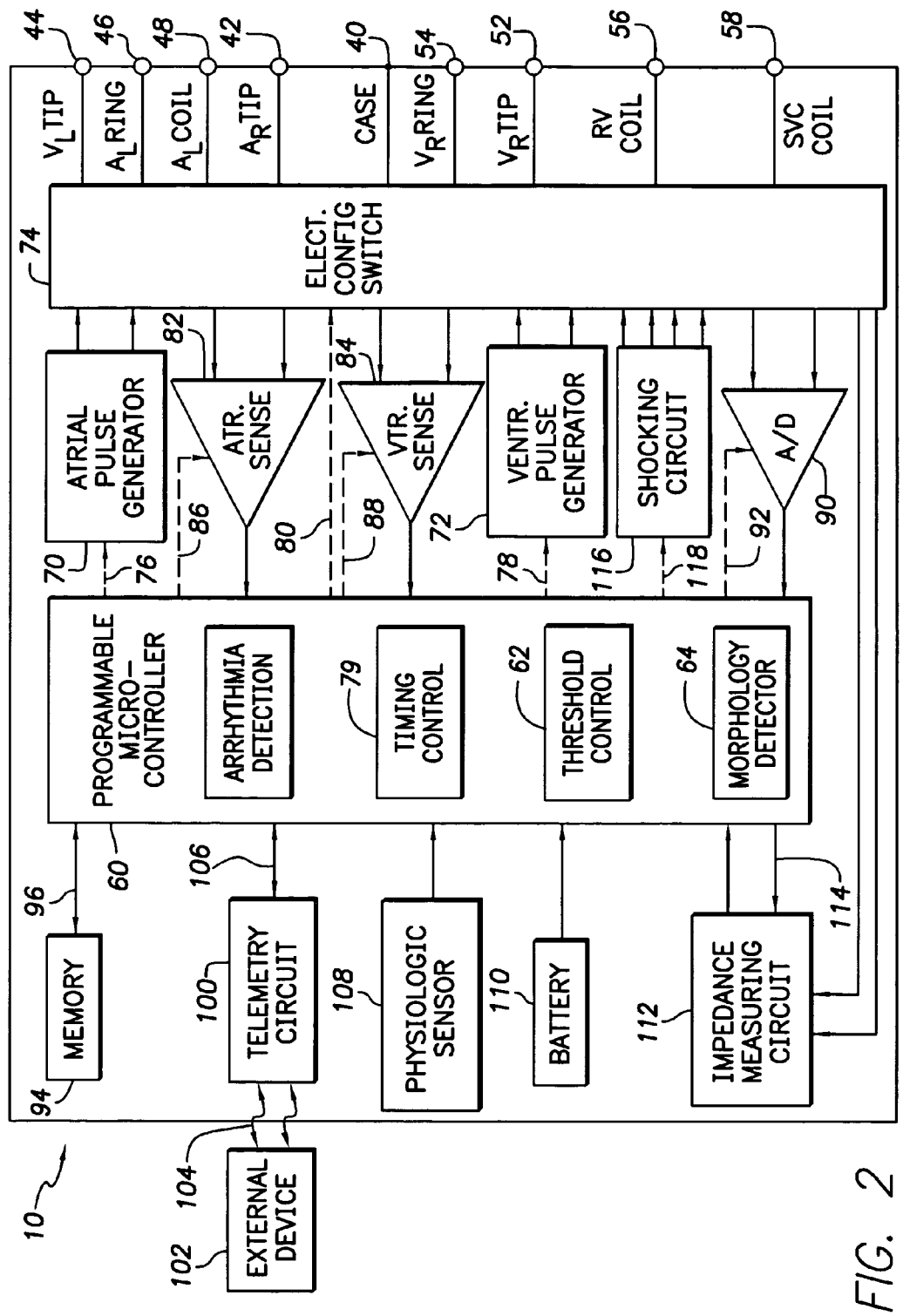
FIG. 2 is a functional block diagram of a multi-chamber implantable stimulation device according to one illustrative embodiment.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the sensing threshold of the sensing circuits, 82 and 84. The threshold control of sensing circuit 84 is preferably carried out in a manner described subsequently herein.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 includes sensing circuits configured to acquire intracardiac electrogram signals, and data processing circuits to convert the raw analog data into a digital signal, and store the digital signals for later processing. Such processing may include, for example, the data processing illustrated in the flow chart of FIG. 4 to provide sensing threshold control. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. The memory 94 may further be employed to store the data (e.g., from the data acquisition system 90), which data may then be used for subsequent processing to determine sensing threshold control parameters.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. The physiologic sensor 108 may be further employed to rate adaptively set a detection window of the data acquisition system 90 for sensing the QRS and T waves required by the threshold control 62. The physiological sensor 108 may still further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 includes an impedance measuring circuit 112 which is enabled by the microcontroller 60 via a control signal 114. The impedance measuring circuit 112 is not critical and is only shown for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, this description shall now turn more specifically to an embodiment of the implantable stimulation device. To this end, it will be noted from FIG. 2 that the device 10 further includes threshold control 62 and a morphology detector 64.

As previously mentioned, the threshold of the sensing circuit 84 is controlled over line 88 to enable the sensing circuit 84 to sense R waves while also enabling the sensing circuit 84 to avoid sensing noise and most importantly T waves which may otherwise be mistaken for R waves. In one illustrative embodiment, the threshold control 62 processes data collected from a sensed and rectified electrogram of a previous cardiac cycle to determine the threshold control during a current cardiac cycle. Of particular importance is data associated with the peak amplitude and location of the T wave of the previous cardiac cycle. Also of importance is the peak amplitude, location, a time of first sensing of the R wave of the previous cardiac cycle. The previous cardiac cycle is preferably the closest preceding intrinsic cardiac cycle.

Figure 3:
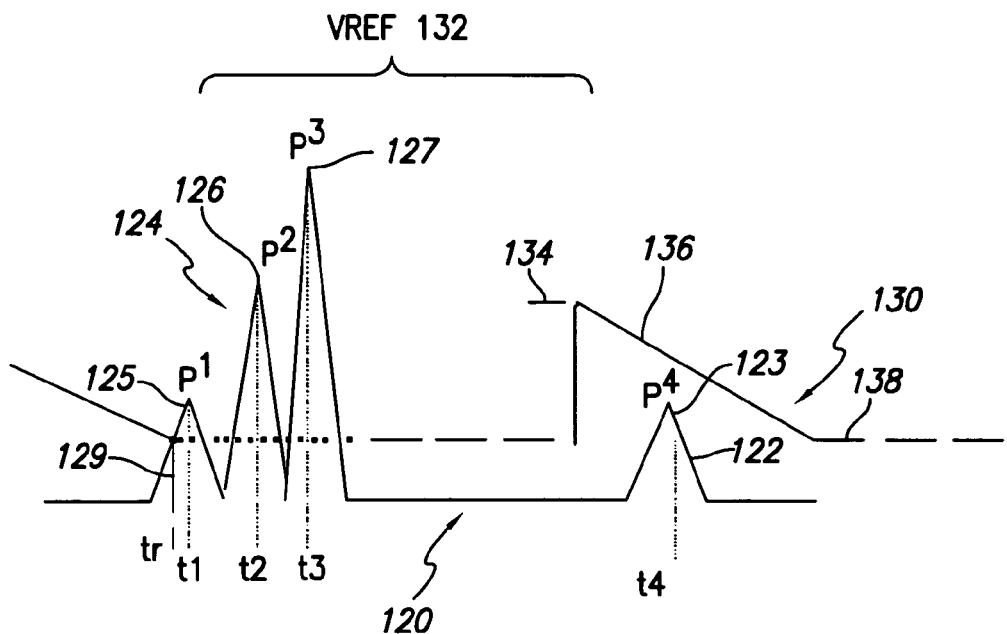
FIG. 3 shows an electrogram of an intrinsic cardiac cycle with a controlled threshold superimposed thereon and which results from the illustrated electrogram in accordance with an illustrative embodiment.

FIG. 3 shows a rectified electrogram 120 of a previous cardiac cycle and the sensing threshold control waveform 130 to be used during a current cardiac cycle to control the threshold of sensing circuit 84 and which results from the data processing of the electrogram 120. Once the electrogram 120 is digitally stored in memory 94, the morphology detector 64 measures the peak amplitude and location of the T wave 122. In one embodiment, an event is identified as a T wave peak as long as its location defines a QT interval greater than a predetermined minimum QT interval (QT min). Preferably, the peak amplitude and location of the R wave 124 are measured.

Typically, the R wave 124 includes three peaks 125, 126, and 127 having values P1, P2, and P3. The location of the R wave (RT) is the location of the peak amplitude. In FIG. 3, the location of peak 127 at time t3 is the R wave location (RT). The R wave peak amplitude (RP) is the value P3.

Similarly, the morphology detector 64 measures the peak amplitude and location of the T wave 122. The T wave 122 has one peak 123 with amplitude P4. Hence, the T wave peak amplitude (TP) is P4 and the location of the T wave (TT) is t4.

The peaks 123, 125, 126, and 127 may be determined in a manner well known in the art. For example, the peaks may be found by calculating slopes. When a slope changes sign, a peak is determined. The peaks may also be found, in accordance with further embodiments, by periodically sampling the electrogram. When a point is found to have a value greater than the value of the points on either side, a peak will be considered to be found. Preferably, for each peak, five points may be sampled. If the center point is greater than any of the other points, the center point is taken as the peak. Alternatively, if the maximum peak is not the first peak or the last peak, then that maximum peak may be considered the peak value even though it may not be the center peak. A further method of finding the peaks is to apply varying thresholds to the stored electrogram. In the case where there are two peaks of equal value and greater than any other peaks, the first such peak may be used for the peak amplitude and peak location.

Lastly, the first sensing time 129 (tr) is determined. This time may be determined as the time of the first data value stored in memory.

With the T wave peak (TP), the T wave location (TT), the R wave peak (RP), the R wave location (RT), and tr determined, the threshold control 62 may now determine the threshold control waveform 130 to be used to control the sensing threshold during the current cardiac cycle.

The first parameter to be determined is a refractory period 132 (VREF). During this time, anything sensed by the sensing circuit 84 is ignored. Alternatively, sensing may be defeated altogether during this time.

The refractory period may be determined by:

$$VREF = (TT-RT) \times K + (RT-tr)$$

where TT is the T wave location (t4 in FIG. 3), RT is the R wave location (t3 in FIG. 3), and K is a factor which may be 0.8 to 1.0.

The factor (K) may be imposed to assure that sensing begins before the T wave 122. However, sensing may begin during the T wave as well.

The next parameter to be determined is the starting threshold 134 (th start). The starting threshold may be determined by:

$$th\ start = (RP-TP)Y + TP$$

where RP is the peak amplitude of the R wave (value P3 in FIG. 3), TP is the peak amplitude of the T wave (value P4 in FIG. 3), Y is a factor preferably between about 0.2 and about 0.5, and RP is greater than TP.

If RP is less than TP, then th start=TP*Z, where Z is preferably between about 1.2 and about 1.8.

The last parameter to be determined is the slope 136 of the linear change in the threshold from the starting threshold 134 to the lowest or most sensitive threshold 138 (th_min). The slope may be determined by:

$$slope = (th\ start - th\_min)/(TT+150\ ms - (VREF+tr))$$

TT+150 ms is an estimated end of the T wave. Alternatively, an intercept may be employed as known in the art to determine the end of the T wave directly.

The above slope does not return the sensing circuit 84 to maximum sensitivity until well after the T wave 122.

With the threshold parameters thus set, the threshold is now controlled by them during the cardiac cycle. In one embodiment, during this current cardiac cycle, the data acquisition system 90 generates new data from the current electrogram to be used to determine new threshold control for sensing heart activity of the next cardiac cycle. Alternatively, the threshold control determinations can be done periodically, such as hourly, daily, etc., or can be done when the system determines that potential T-wave oversensing is occurring, or both.

Figure 4:
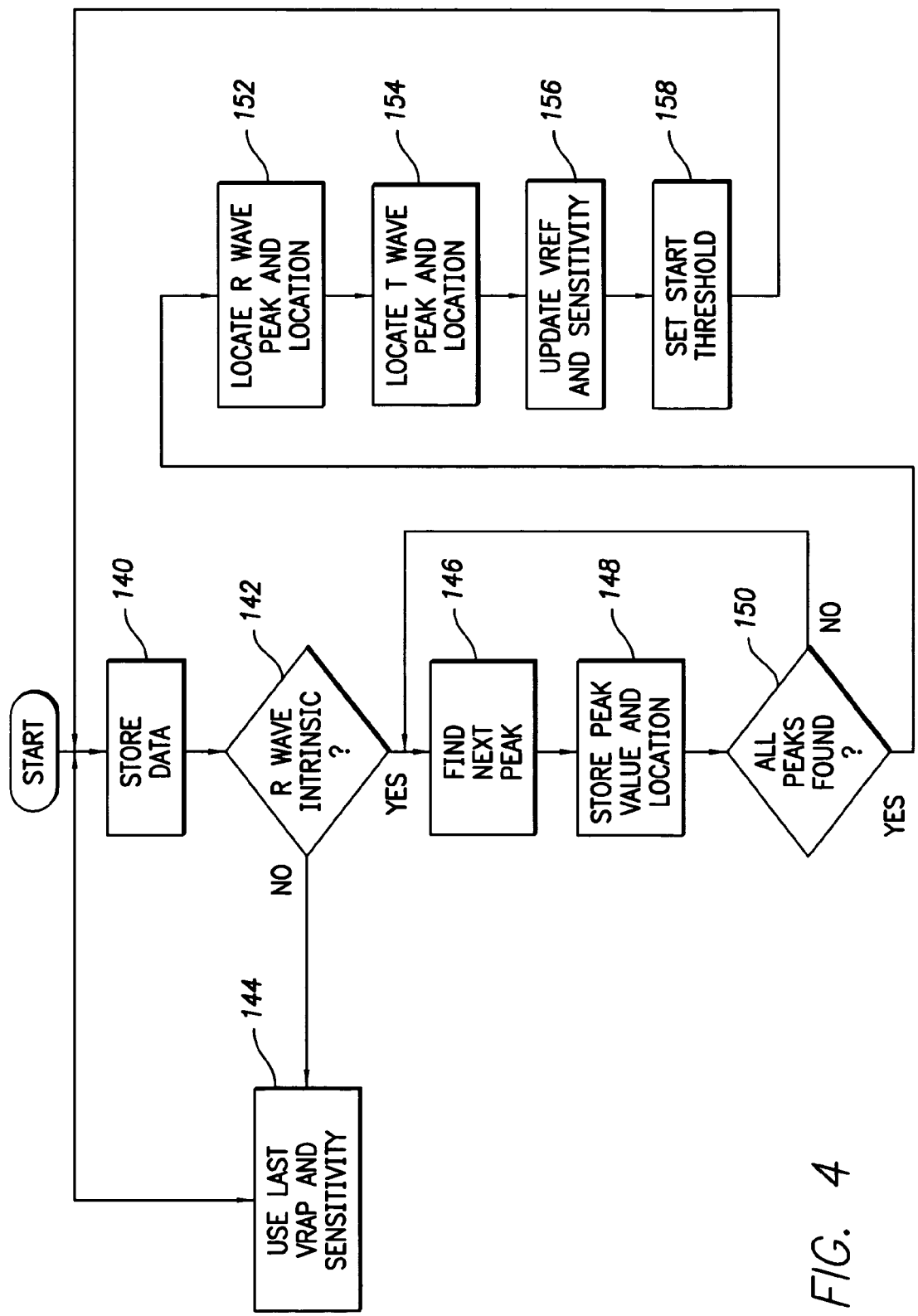
FIG. 4 is a flow chart describing an overview of the operation of one embodiment of the implantable stimulation device.

FIG. 4 illustrates a flow chart illustrating the overall operation of the threshold control system according to one illustrative embodiment.

The threshold control of FIG. 4 may be initiated after a time-out of a programmable period such as daily or every eight hours, etc. as determined by the timing control 79. The process begins with activity block 140 wherein data is stored by the data acquisition system 90 during a previous cardiac cycle. Once the data is stored, the process advances to decision block 142 which determines if the R wave of the last cardiac cycle was an intrinsic R wave. If the R wave is not an intrinsic R wave, the process immediately advances to activity block 144 wherein the threshold control 62 sets the threshold control parameters to the last set of threshold control parameters. The process then returns.

However, if the R wave was an intrinsic R wave, the process advances to activity block 146 wherein the morphology detector 64 begins to locate the various peaks of the electrogram. As a result, the morphology detector finds the next peak in the electrogram which may be the first peak. Once the peak is found in activity block 146, the process advances to activity block 148 wherein the threshold control 62 stores the peak amplitude and location of the peak located in activity block 146. Once the peak value and location is stored in activity block 148, the process advances to decision block 150 wherein it is determined if all peaks have been found. If all peaks have not been found, the process returns to activity block 146 for the finding of the next peak in the electrogram.

If in decision block 150 it is determined that all peaks have been found, the process advances to activity block 152. Here, the morphology detector locates and measures the peak amplitude of the R wave (RP) which has value P3 and the location of the R wave (RT) which is t3. After the R wave peak and location are stored, the process advances to activity block 154 wherein the morphology detector measures the peak amplitude of the T wave TP which is value P4 and the location of the T wave (TT) which is t4.

With the R wave peak, the R wave peak location, the T wave peak, and the T wave peak location all being measured, the process then advances to activity block 156 wherein new refractory period and sensitivity values are determined as previously described. More specifically, the refractory period VREF and the sensitivity parameters including the starting threshold and threshold slope are determined. The process then advances to activity block 158 where the newly determined threshold control parameters are set for use during the next cardiac cycle. The process then returns. A new threshold curve 130 may be determined from a single cardiac cycle. Alternatively, a new or updated threshold curve may be an average curve, averaged over a few cardiac cycles.

Still further, the new sensitivity threshold values may be compared to an average of previous values, such as a running average. If the new values differing from the average values by more than a certain amount may be used to trigger the updating with the new values.

Thus far, the illustrated embodiments herein have been directed towards developing a time running sensing threshold for only intrinsic cardiac activity. As will be seen subsequently, the implantable stimulation device may be employed to advantage for setting the sensitivity threshold parameters based also on paced cardiac activity.

Figure 5:
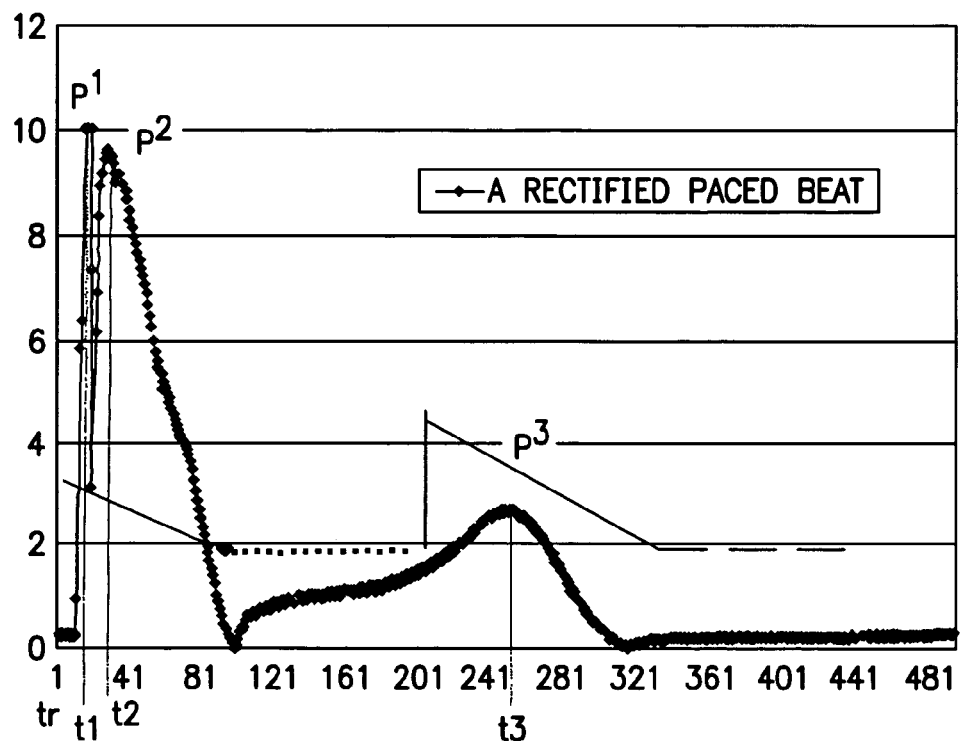
FIG. 5 shows an electrogram of a paced cardiac cycle and a resulting controlled threshold according to another embodiment of the implantable stimulation device.

FIG. 5 is a rectified waveform of a paced cardiac cycle. In connection with paced cardiac cycles, the values of R wave peak (RP), R wave location (RT), T wave peak (TP), T wave location (TT) and initial sense time (tr) may be determined in the same manner as previously described with respect to intrinsic cardiac cycles, such as that shown in FIG. 3. Hence, for the paced cardiac of FIG. 5, the R wave peak (RP) has a value of P1, the location of the R wave (RT) has a value of t1, the T wave peak (TP) has a value of P3, and the T wave location (TT) has a value t3. These measured values may be used to determine new sensitivity threshold parameters of VREF, th start, and slope as previously described.

Figure 6:
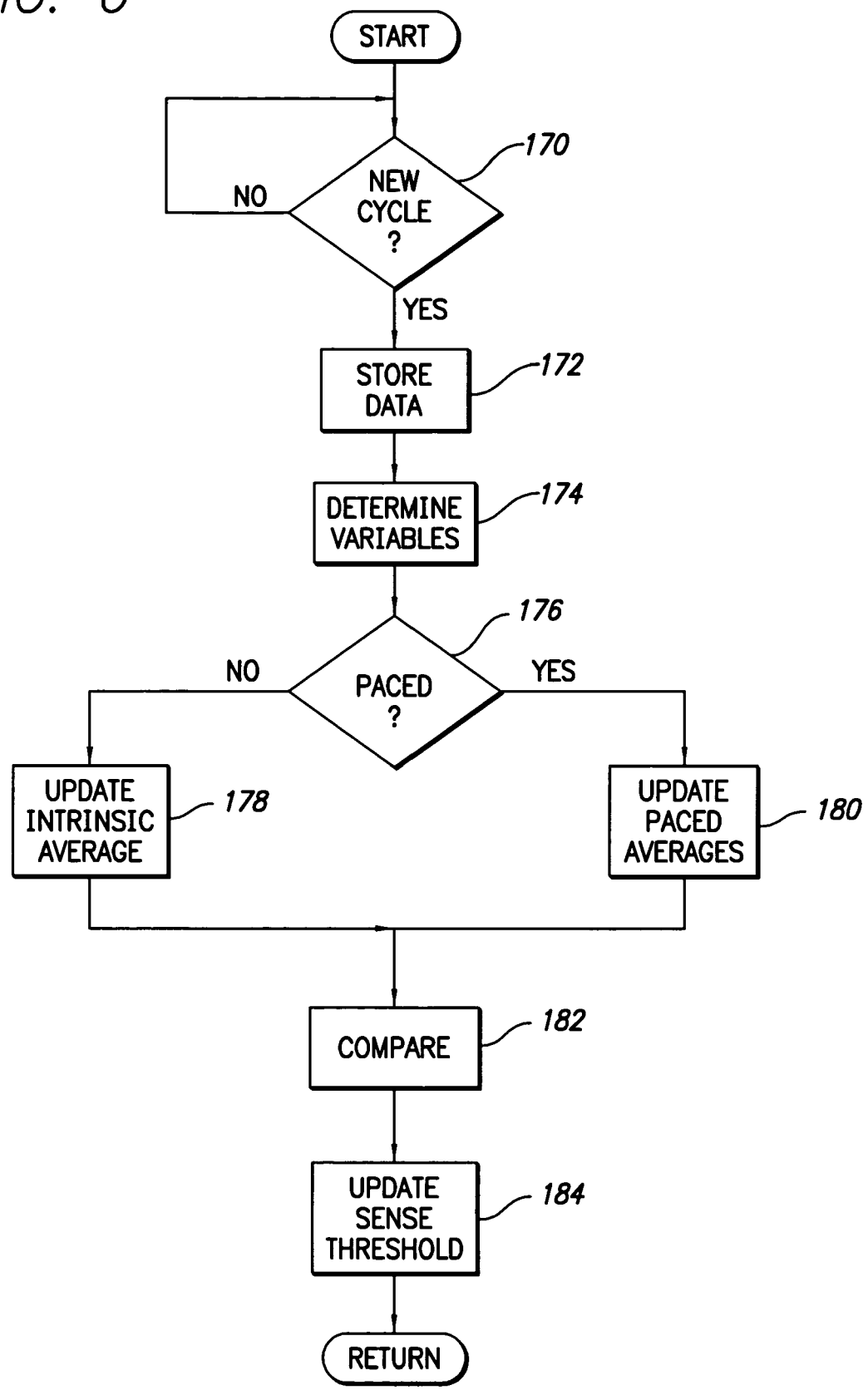
FIG. 6 is a flow chart of an embodiment of the implantable stimulation device for both intrinsic and paced cardiac cycles.

FIG. 6 shows a flow chart describing an embodiment wherein both intrinsic and paced cardiac cycles are considered for setting new sensitivity parameters. The process begins with decision block 170 wherein it is determined if a new cardiac cycle has begun. When a new cardiac cycle begins, the process advances to activity block 172 where the cardiac activity data is stored for the cardiac cycle by the acquisition system 90.

The process then advances to activity block 174 where the data stored in activity block 172 is used to determine new values for R wave peak (RP), R wave location (RT), T wave peak (TP), T wave location (TT) and refractory period (VREF). These values may be determined as previously described.

The process next advances to decision block 176 where it is determined if the last R wave and T wave were intrinsic or paced. If intrinsic, the process advances to activity block 178 where the new values of VREF, RF, RT, TP, and TT are used to update a running average of these values for intrinsic activity. Similarly, if the last R wave and T wave resulted from a pacing pulse, the process advances to activity block 180 where the new paced VREF, RP, RT, TP, and TT are used to update a running average of these values for paced activity.

Now, in activity block 182 the new values of RP, RT, TP, TT and VREF may be compared to a previous value or to the average values to determine if the sensitivity threshold parameters need to be changed. For example, a T wave peak (TP) resulting from a pacing pulse may be compared to the last determined intrinsic T wave peak. Then, when the sensitivity threshold parameters are updated, the greater of the two may be used. This comparison may also be done for VREF with the greater value being used for updating.

Still further, the comparisons in activity block 182 may be used to trigger a sensitivity update. For example, new intrinsic values of RP, TP and/or VREF may be compared to intrinsic average values. An update in sensitivity parameters may then be triggered if there is a change in these values. The same process may be performed for paced values of RP, TP and/or VREF as well to trigger a parameter update.

Once activity block 182 is completed, the process advances to activity block 184. Here the sensitivity threshold parameters are updated if required. The process then returns.

The process of FIG. 6 may be implemented on a beat to beat basis. Alternatively, the process of FIG. 6 may be implemented at spaced apart times are triggered by a specific event.

The foregoing may further be used to advantage in atrial sensing. Here, the sensitivity threshold parameters may be set to avoid sensing a far field R wave and mistaking it for a P wave. In accordance with this embodiment, the P wave peak and location may be substituted for the R wave peak and location and the far field R wave peak and location may be substituted for the T wave peak and location. With these substitutions, the sensitivity threshold parameters for atrial sensing may be determined and updated as previously described.

While specific embodiments have been described, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   a sensing circuit that senses cardiac activity of a heart using a time-varying sensing threshold that varies during each cycle, wherein the cardiac activity includes T-wave activity;
   a pulse generator that applies electrical energy to the heart in response to the sensed cardiac activity of the heart; and
   a threshold control comprising a detector that determines a plurality of morphological characteristics of the T-wave activity and that adjusts the time-varying sensing threshold of the sensing circuit in response to the determined morphological characteristics of the T-wave activity.

2. The device of claim 1 wherein the sensing circuit senses ventricular activity and wherein the plurality of morphological characteristics include T wave amplitude and duration.

3. The device of claim 2 wherein the T wave characteristics include T wave location.

4. The device of claim 2 wherein the detector further determines a plurality of R wave characteristics of the cardiac activity and wherein the threshold control varies the sensing threshold in response to the determined T wave characteristics and the determined R wave characteristics.

5. The device of claim 1 wherein the detector determines the morphological characteristics of intrinsic cardiac activity.

6. The device of claim 1 wherein the detector determines the morphological characteristics of intrinsic and paced cardiac activity.

7. The device of claim 6 wherein the threshold control compares determined morphological characteristics of paced cardiac activity to determined morphological characteristics of intrinsic cardiac activity prior to varying the sensing threshold.

8. The device of claim 1 wherein the sensing circuit is an atrial sensing circuit that senses atrial activity and wherein the threshold control varies the sensing threshold to preclude sensing of far field R waves by the atrial sensing circuit.

9. The device of claim 8 wherein the morphological characteristics include far field R wave amplitude and far field R wave location.

10. In an implantable cardiac stimulation device, a method of determining a time-varying sensing threshold waveform that varies during each cycle, the method comprising:
    sensing cardiac activity of the heart, including T-wave activity;
    measuring a plurality of morphological characteristics of the T-wave activity; and
    defining the time-varying sensing threshold waveform based upon the plurality of morphological characteristics of the T-wave activity.

11. The method of claim 10 wherein the morphological characteristics comprise T wave amplitude and T-wave duration.

12. The method of claim 11 wherein the morphological characteristics further comprise T wave location.

13. The method of claim 10 wherein the morphological characteristics include R wave characteristics and T wave characteristics and wherein defining the sensing threshold waveform comprises defining the sensing threshold waveform based upon the measured T wave characteristics and the measured R wave characteristics.

14. The method of claim 13 wherein the R wave characteristics include R wave amplitude and R wave location.

15. The method of claim 10 wherein measuring comprises measuring the morphological characteristics of paced cardiac activity.

16. The method of claim 10 and further comprising providing a refractory period responsive to the measured morphological characteristics.

17. An implantable cardiac stimulation device comprising:
    means for sensing cardiac activity of a heart;
    means for measuring two or more T-wave characteristics of the cardiac activity; and
    means for defining a time-varying sensing threshold waveform that varies during each cycle as a function of the two or more T-wave characteristics.

18. The device of claim 17 wherein the means for defining comprises means for processing T wave amplitude and duration to define the sensing threshold waveform.

19. The device of claim 17 wherein the means for defining comprises means for defining a time-varying sensing threshold waveform as a function of the two or more T-wave characteristics.

20. The device of claim 17 wherein the means for measuring comprises means for measuring T-wave characteristics and R-wave characteristics.

* * * * *